(12) United States Patent
Tanielian (10) Patent No.: US 7,410,805 B2
(45) Date of Patent: Aug. 12, 2008

(54) AEROSOL DETECTION SYSTEM USING OPTICAL AND MASS DISCRIMINATION

(75) Inventor: Minas Tanielian, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 917 days.

(21) Appl. No.: 10/630,400

(22) Filed: Jul. 30, 2003

(65) Prior Publication Data

US 2008/0171398 A1 Jul. 17, 2008

(51) Int. Cl.
*G01N 1/18* (2006.01)

(52) U.S. Cl. .................. 436/177; 436/56; 436/165; 436/172; 436/174

(58) Field of Classification Search ............. 422/82.01, 422/82.02, 82.05, 82.08, 83, 88, 98; 436/149, 436/164, 167, 172, 177, 178, 56, 165, 174
See application file for complete search history.

(56) References Cited

U.S. PATENT DOCUMENTS

| | | | | |
|---|---|---|---|---|
| 5,674,698 A | * | 10/1997 | Zarling et al. | 435/7.92 |
| 6,391,624 B1 | * | 5/2002 | Megerle | 435/287.2 |
| 6,484,594 B1 | | 11/2002 | Saaski et al. | |
| 6,532,835 B1 | | 3/2003 | Saaski et al. | |
| 7,062,982 B2 | * | 6/2006 | Coyle et al. | 73/863.23 |
| 2002/0175294 A1 | | 11/2002 | Lee et al. | |

FOREIGN PATENT DOCUMENTS

| | | |
|---|---|---|
| WO | WO 02/052246 A2 | 7/2002 |
| WO | WO 03/005446 A1 | 1/2003 |

* cited by examiner

*Primary Examiner*—Jill Warden
*Assistant Examiner*—Dwayne K Handy
(74) *Attorney, Agent, or Firm*—Harness, Dickey & Pierce, P.L.C.

(57) ABSTRACT

A system to detect and identify various aerosol agents, such as biological agents which have been aerosolized, is disclosed. The system generally includes a mechanism to collect a selected sample of atmosphere which may include the aerosol agent, a sub-system to detect the presence and type of agent, and a sub-system to communicate the type of agent detected.

27 Claims, 2 Drawing Sheets

Figure 4

AEROSOL DETECTION SYSTEM USING OPTICAL AND MASS DISCRIMINATION

FIELD OF THE INVENTION

The present invention relates generally to detection of aerosolized materials; and particularly to aerosolized materials that may cause injury, sickness, or death.

BACKGROUND OF THE INVENTION

Many agents, such as chemicals, microbes, including spores and bacteria, and viruses can be extremely harmful or discomforting to living organisms, such as humans, if they are able to infect the living organism. These various harmful agents may either be naturally occurring or synthesized by various techniques. Certain viruses, bacteria, or natural toxins may be naturally occurring, but can also be refined, enhanced, or bred, to become greatly more harmful to the living organism.

Generally, the more refined or harmful organisms or agents are used for weapon uses. For example, various toxins can be synthesized or refined to become weaponized for various applications. The toxins may be weaponized and dispersed from a missile over a selected area. Similarly, most agents, can also be weaponized for various applications. The areas affected by the weaponized agents succumb to the various agents that were placed in the weapon delivery system.

The agents may be released in various locations, other than by use of missiles or other projectiles. For example, pressurized canisters may be used to deliver the various agents. Therefore, the agents can often be released into areas which are otherwise unsuspecting of an agent attack. In addition, the aerolized agents are often invisible to the naked eye and particularly difficult to detect before infection. Therefore, it is desirable to provide a mechanism and system that will allow for easy and quick detection of the various agents.

Particularly, it is desirable to detect and confirm the presence of various aerosol agents in a selected period of time. Generally, it is desirable to detect the agents before the agents have been able to infect individuals and cause injury thereto. This is particularly the case in civilian areas where the presence of weaponized agents is not necessarily expected. Therefore, the detection of the agents is generally desired to be substantially quick and easy to use and have a high degree of reliability.

SUMMARY OF THE INVENTION

A system to detect and identify various aerosol agents, such as biological agents which have been aerosolized, is disclosed. The system generally includes a mechanism to collect a selected sample of atmosphere which may include the aerosol agent, a sub-system to detect the presence and type of agent, and a sub-system to communicate the type of agent detected.

Generally, the aerosol detection system includes a first portion to ingest or collect a selected quantity of atmosphere in which the aerosol agent may exist. A second portion of the system is able to collect or concentrate particles from the atmosphere collected into a sample size that is manageable for the detection system, particularly for the speed and accuracy required. The agent aerosol detection system also includes a further portion to interact with the concentrated sample to detect or collect any aerosolized agents therein. The aerosol agent detection system is also able to distinguish between the various particles or agents that are collected in the sample. Finally, the system is able to communicate the detected aerosolized agents to provide a feedback to a user.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses.

Figure 1:
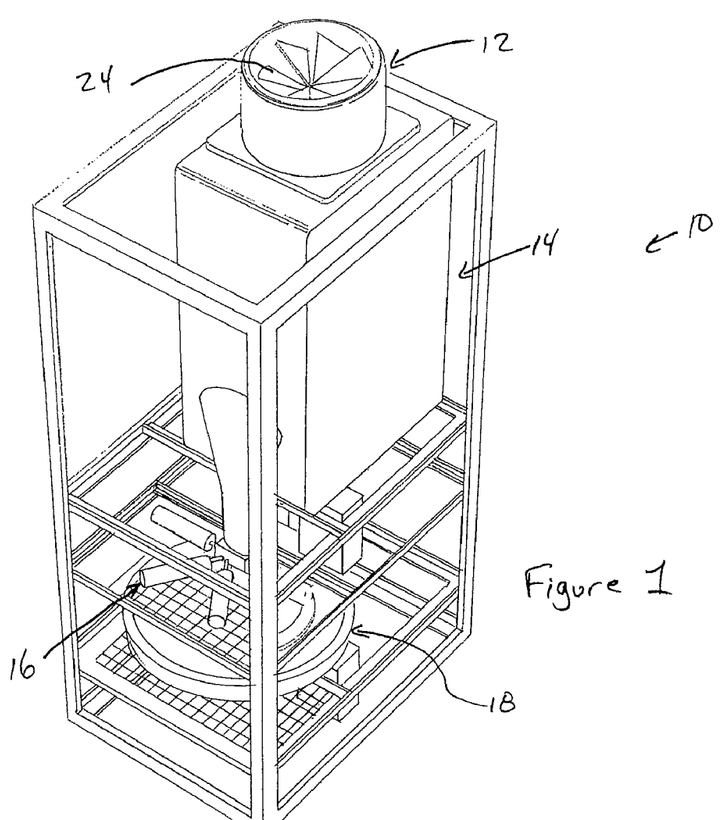
FIG. 1 is a prospective view of an aerosol agent detection system.

With reference to FIG. 1, a bio-aerosol detection system 10 is illustrated. The system 10, is generally able to collect a sample of the atmosphere surrounding the apparatus 10 to form an atmospheric sample. The apparatus 10 may be able to concentrate agents of interest in the sample and detect the presence of various agents. Although the atmospheric sample need not necessarily be concentrated. It will be understood that the following description is merely exemplary, and not intended to limit the scope of the various components of the system 10. The system 10, includes the components to collect and determine whether an agent is present in the atmospheric sample. The system 10 is also able to determine and distinguish a plurality of types of the agents.

Generally, the system 10 includes an atmospheric collection sub-system 12 that is able to collect a selected volume of an atmosphere. The atmosphere collected can be any appropriate atmosphere, such as the atmosphere of a building, the atmosphere of a vehicle, or a localized atmospheric condition. It will be understood that the atmospheric sample collected generally includes the gases present in the atmosphere (herein referred to as air) and other particles present in the atmospheric sample. The agents of interest in the sample can include bacteria, spores, dust, various chemical compositions such as toxins, and other components. The agents of interest are generally and inclusively referred to as agents herein. Alternatively, the atmosphere collection sub-system 12 may be modified to collect only the portions of the atmosphere necessary to determine presence of a selected agent or agents.

Operably interconnected with the atmospheric collection sub-system 12 is a concentration sub-system 14. The concentration sub-system 14 is generally able to concentrate a selected portion of the atmosphere collected with the atmosphere collection sub-system 12. Any appropriate system may be used to concentrate the selected portion of the atmosphere collected with the atmosphere collection sub-system 12, and various examples are described herein. Regardless, the atmospheric sample concentration sub-system 14 is able to concentrate a selected portion of the atmosphere drawn in through the atmosphere sample collection sub-system 12. Specifically, the concentration sub-system 14 is able to concentrate any agents present in the sample therefore the entire sample need not be analyzed or the sample size may be small.

The concentration sub-system 14 may include any appropriate configuration. For example, the concentration sub-system 14 may be a substantially dry concentration sub-system or a wet concentration sub-system. That is, the atmospheric sample can be drawn in and concentrated without adding a substantial amount of moisture or a liquid. Alternatively, the atmospheric sample may be drawn into and concentrated in a solvent or liquid. Various aqueous, basic, acidic, or ionic solvents may be used to dissolve the atmospheric sample and assist in later concentration.

It will be understood that the concentration sub-system 14 is not required. For example, the collection sub-system 12 may simply draw a selected amount of the atmosphere into an atmosphere collection or containment area. The concentrator sub-system 14 may be eliminated to simply test an entire sample or when various procedural concerns are not necessary to be considered. Therefore, it will be understood that the concentration sub-system 14 is not a necessary component of the detection system 10.

The atmospheric sample concentration sub-system 14 is interconnected with a tagging or sensing sub-system 16. The tagging sub-system 16 generally allows for an interaction of a selected agent from the concentrated sample from the sample concentrator 14 to be later analyzed. The tagging system 16 may be any appropriate tagging system depending upon the requirements of the aerosol detection system 10. For example, the tagging sub-system 16 may interact with a substantially dry or non-dissolved sample from the sample concentrator 14. Therefore, the tagging sub-system 16 can interact and tag various agents in the concentrated dry sample without substantially changing the constitution of the sample.

Alternatively, the tagging sub-system 16 may introduce a liquid to the concentrated sample from the sample concentration sub-system 14. Alternatively, the tagging sub-system 16 may simply add a fluid including a selected tag to the concentrated sample from the sample concentration sub-system 14. Regardless, the tagging sub-system 16 is able to tag or interact with the various selected agents that may be present in the concentrated sample from the sample concentration sub-system 14.

Any appropriate tag may be used to interact with the sample from the sample concentration sub-system 14. For example, various molecules may be present to interact with the agents that are present in the concentrated sample from the sample concentration sub-system 14. The molecules or tags are then able to be detected by the aerosol detection system 10. Alternatively, the tag may be a particle that interacts with the selected agents. Regardless, various tags may be provided to interact with the agent that may be present in the sample of the atmosphere.

The tags may also be used later for various separation techniques, such as mass separation, electrophoresis, dielectrophoresis, solvent/gel interaction, and various other known or appropriate techniques for determining the presence of the selected agents. It will be understood that the tagging sub-system 16 is not limited to any particular system but can include any appropriate tagging sub-system.

In addition, the aerosol detection system 10 also includes a separation and analysis sub-system 18. The analysis and separation sub-system 18 generally includes a separation portion 18a and an analysis or detection portion 18b. The separation and analysis sub-system 18 is able to determine the presence of selected agents that may be present in the concentrated atmospheric sample. Again, the analysis and separation sub-system 18 may be any appropriate analysis and separation sub-system 18 for the aerosol detection system 10, depending upon the various selected characteristics. For example, the analysis and separation sub-system 18 may separate the selected portions of the sample using a liquid base or method. The liquid based sub-system may use a selected liquid chromatography to interact with the tags added in the tagging sub-system 16 to separate or determine the presence of any selected agents. Alternatively, various electrophoresis, dielectrophoresis or channel separation systems may be applicable in the analysis of the separation sub-system 18. In addition, the analysis and separation sub-system 18 may be a substantially dry system or include interaction of the separation sub-system 18 with a liquid. Therefore, the separation and analysis sub-system 18 may include any appropriate functions or portions depending upon the specifics of the characteristics of the concentrated sample in the sample concentration sub-system 14.

As a further example, if the sample is substantially dry, various dry electrophoresis or dielectrophesis interactions may be used to separate the particular agents. In addition, various centrifugal forces may be applied to further separate the selected agents from the concentrated atmospheric sample. Therefore, it will also be understood that one or a plurality of separation techniques may be used in the separation and analysis sub-system 18 to achieve selected goals or characteristics of the detection system 10. Further, a plurality of separation techniques may be used at once to separate the agents.

The analysis portion 18b of the analysis and separation sub-system 18 is able to determine, according to various parameters and techniques, the presence and the identity of various selected agents from the concentrated atmospheric sample. For example, the tag applied to the atmospheric sample may include a selected and detectable property. A detectable property may include various forms of radiation that may be emitted by the tag applied in the tagging sub-system 16 that may be detected in the analysis portion 18b of the analysis and separation sub-system 18.

As an example, the tags added in the tagging sub-system 16 may emit visible, infrared, or ultraviolet radiation. This specific wave length of the various radiations being equivalent or determined to be related to a selected agent from the concentrated atmospheric sample. Therefore, the analysis portion 18b is able to detect a given radiation output which leads to a determination regarding the presence of various agents. Nevertheless, it will be understood that any appropriate analysis portion 18b may be included in the analysis and the separation sub-system 18. For example, various mass separation determinations may be used depending upon the separation portion 18a. Also, detecting a selected radiation or a selected wave length of a selected radiation is merely exemplary and is not intended to limit the scope of the present disclosure and appended claims.

The aerosol detection system 10 is able to be used to determine and identify various agents that may be present in an atmospheric area or sample. The various portions of the aerosol detection system 10 may include various exemplary portions, as described herein. Nevertheless, it will be understood that the various exemplary embodiments described herein are not intended to limit the scope of the appended claims, but are made simply to provide identification for various embodiments envisioned.

The atmospheric sample intake sub-system 12 may be any appropriate intake sub-system. For example, and as illustrated in FIG. 1, the atmospheric sample sub-system intake 12 may include a fan 24. The fan 24 may be driven by any appropriate motor that is internal or external to the atmospheric intake sub-system 12. The fan 24 is able to draw air from the exterior of the system 10 and drive it into the atmospheric sample concentrator sub-system 14.

The atmospheric intake sub-system 12, may also be selected depending upon various selected characteristics of the atmospheric detection system 10. For example, it may be desired to collect a selected volume of atmosphere in a given time span. Therefore, the size or the speed of the atmospheric collection sub-system 12 may be selected to achieve these various results. In addition, the size of the atmospheric collection sub-system 12 can be selected for various physical constraints. For example, it may be desired to provide the atmospheric detection system 10 within a selected volume thus requiring the atmospheric intake sub-system 12 to require no more than a given volume.

The atmospheric intake sub-system 12 is generally able to intake a selected volume of the atmosphere surrounding the system 10 and provide it to the atmospheric sample concentrator 14 during a selected time period. In addition, the atmospheric intake sub-system 12 is able to provide the selected atmosphere sample to the atmospheric concentrator 14 without substantially contaminating the sample of the atmosphere. Generally, at least one purpose of the system 10 is to determine the presence of unwanted agents in the atmospheric sample. Therefore, providing a generally clean atmospheric intake sub-system 12 may be desirable.

After the atmospheric sample and the selected agents are collected using the atmospheric collection sub-system 12, they are concentrated or moved to the atmospheric air concentration sub-system 14. The atmospheric air concentration sub-system 14, may be any appropriate atmosphere or fluidic concentration system. It will be understood that agents may not always be present, as it is one purpose of the system 10 to so determine. Nevertheless, the following description generally assumes the presence of such agents for discussion of the system 10.

The complexity of the concentration sub-system 14 may range from a simple volume to a collection and concentration system such as a cyclonic air sampler. Various cyclonic air samplers are generally known, such as the system disclosed in U.S. Pat. No. 6,532,835 entitled "High Efficiency Wetted Surface Cyclonic Air Sampler", incorporated herein by reference for all purposes. The wetted surface cyclonic sampler may be useful if the sample is collected into a liquid solution or liquid for later detection and analysis. Therefore, the atmospheric collection sub-system 12 may collect the selected sample and place it into a solution of a liquid for concentration or initial separation in a cyclonic sampler. Without great detail, the wetted cyclonic sampler is generally able to strip or collect the selected agents from the atmospheric sample. The stripped agents may be concentrated in the wetted portion of the concentrated sub-system 14 for later analysis and detection.

Although the wetted cyclonic concentration system may be used for the atmospheric sample concentration sub-system 14, it may not be one of the characteristics of the detection system 10 to include a liquid in the detection system 10. Therefore, the sample concentration sub-system 14 may also be a substantially dry sub-system. That is, the moisture or liquid content within the sample collected by the sample collection sub-system 12 is not substantially wet or high in moisture and may even be dried before entering into the concentration sub-system 14. Therefore, the concentration sub-system 14 may also include a volume into which the atmospheric sample may be placed. That is, a selected volume of the atmosphere surrounding the system 10 can be drawn in with the atmosphere collection sub-system 12 and placed in the sample concentration sub-system 14.

The volume placed in the concentration sub-system 14 of the atmosphere collected by the atmospheric collection sub-system 12 may be a volume great enough to provide a sufficient amount of the selected agent, if present, for later analysis. That is, the volume would include a critical amount or selected amount of the agent if present in the atmosphere. Therefore, rather than concentrating the agent, which may be present in the atmospheric sample concentrated in the atmospheric sample and concentrator 14, simply enough of the atmosphere is drawn into the sample concentrator 14 for later analysis. As an example, if an absolute number of at least 1000 parts of the agent are necessary for accurate detection either the sample may be concentrated or a larger amount of the sample may be analyzed.

After the appropriate amount of the sample is transferred in an appropriate fashion, to the tagging sub-system 16, the atmospheric sample may be transferred from the concentration sub-system 14 to the tagging sub-system 16 in an appropriate manner such as blowing or mass transfer. It will be understood that if the system 10 is substantially a dry system, that the sample may be blown or drawn using a vacuum or pressure differential from the sample concentration sub-system 14 to the tagging sub-system 16. Alternatively, if the sample concentrator 14 or the system 10 in general is a substantially liquid or wet system, the material may be moved using a pump or other appropriate method. It will be understood, that the liquid for the system 10 may be any appropriate liquid. "Wet" also generally, as used herein, refers to the presence of a liquid which may suspend the agent that may be present in the atmosphere. Therefore, wet is not simply limited to the presence of water but may also include any other appropriate liquid, such as a organic liquid, acidic or basic liquid, or any other appropriate liquid.

In the tagging system 16, various appropriate mechanisms are present to allow for tagging of the agent present in the sample. It will be understood, although the following description relates generally to a substantially dry tagging technique that any appropriate tagging technique may be used. For example, if the concentrated sample from the sample concentrator 14 is substantially in a liquid a fluid transfer of the sample may be used to transfer the sample to a substantially liquid holding container. In the liquid holding container, the appropriate tags may be applied to the selected agents for later analysis. Nevertheless, the wet system may be substantially similar to the substantially dry system described herein, but rather the sample is contained in the liquid and provided to a substantially liquid environment for later analysis.

Figure 2:
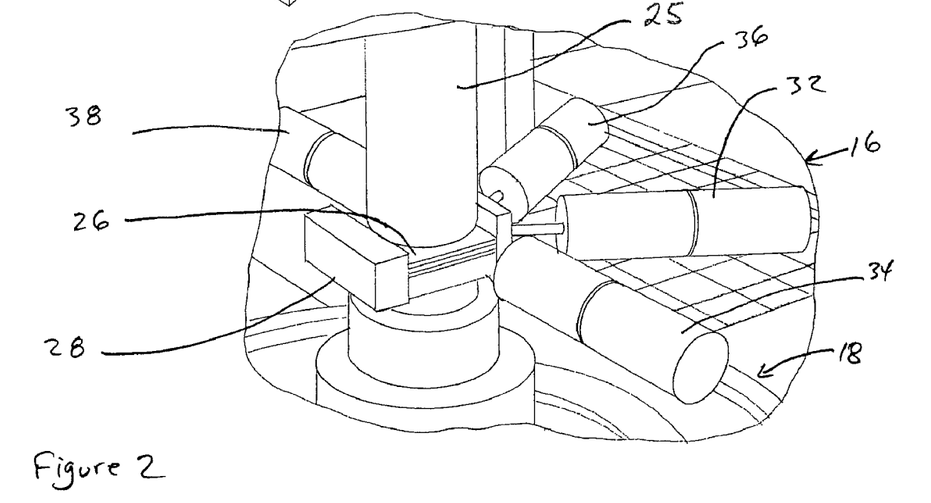
FIG. 2 is a detailed view of a mixing system according to an embodiment of the invention.

With particular reference to FIG. 2, the tagging sub-system 16 is generally positioned operably with an outlet 25 of the sample concentration sub-system 14. The outlet 25 provides the concentrated sample to a mixing cell 26. The mixing cell 26 is generally able to contain the concentrated sample from the sample concentrator 14 for the tagging process. Operably interconnected with the mixing cells 26 is an ultrasonic vibrator or mixer 28. It will be understood that any other appropriate mixer may be provided besides the ultrasonic mixer 28, but size and speed considerations may allow for use of the ultrasonic mixer 28. It will be understood that other mixing processes, such as mechanical, mass distribution, and other generally known mixing apparatii can be used in the mixing chamber 26.

Before, after or substantially in conjunction with providing the sample to the mixing cell 26, a tag and a selected amount of a liquid is provided to the mixing cell 26. At least a single injector 32 is provided to inject an appropriate substance into the mixing cell 26. It will also be understood that a second injector 34, a third injector 56 and a fourth injector 38 may also be provided. In addition, any other appropriate number of injectors may be provided for injecting material into the mixing cell 26. For example, six, eight or any other appropriate number of the injectors 32 may be provided to inject the selected material into the mixing cell 26.

Nevertheless, the injectors 32 are generally able to inject the tags and a selected amount of a liquid into the mixing cell 26. Even if the mixing cell 26 is a substantially dry cell and the system 10 is provided to be a substantially dry system, a selected amount or volume of liquid may be injected into the mixing cell 26. Without being limiting by the theory, it is generally believed that any agent that may be present in the atmosphere sample may better be mixed with the tags in a liquid environment. In addition, various known agents are understood to be provided in a selected weaponized format that substantially only breaks down in the presence of a selected volume of a liquid. Therefore, a selected volume of liquid is injected into the mixing cell 26 to allow access to the weaponized form of the agent that may be present in the atmospheric sample.

The tags supplied in the tagging system 16 are generally intermingled with and connected to the selected agents in the mixing chamber 26. The tags may either be present in the mixing chamber 26 or added to the mixing chamber at any appropriate time. For example, the tags may be injected with the liquid that is injected from the injector 32. Regardless, the tag is able to interact with the agent in the atmospheric sample to become substantially commingled or interacted with the tag.

The tag may be any appropriate tag that may be analyzed in the analysis and separation sub-system 18. As discussed further herein, the tags may include particles that have a selected property to interconnect with a selected agent for analysis and detection at a later time. It will also be understood that other appropriate tags, such as single molecular species and the like may be interconnected with the selected agents that may be present in the atmospheric sample.

Regardless of the tag provided, it is generally more efficient to mix the material or agents than may be present in the atmospheric sample to assure at least a chance for interconnection between the agent of the atmospheric sample and the selected tag. A mixer, such as the ultrasonic mixer 28 may be provided to substantially mix the atmospheric sample from the atmospheric sample concentrator 14 with the liquid injected from the injectors 32, 34, 36 and 38 and the tags. As discussed above, the tags may already be present in the mixing chamber 26 or injected from the injectors. In addition, the mixer 28 may not necessarily be required to be the ultrasonic mixer 28. For example, a fan or physical mixer may be present in the mixing chamber 26 to mix the atmospheric sample and the tags. The liquid may also assist in the mixing within the mixing chamber 26.

It will also be understood that the mixing chamber 26 may include a single type or a plurality type of tags. If a single tag type is included generally only one is interacted and only one agent is detected. If a plurality of types of tags are present then more than one agent may be interacted and identified. For example, a single tag may be provided for a single selected agent, such as a specific bacterium. Alternatively, a plurality of tags may be selected to be present in the mixing chamber 26 for interacting with a plurality of agents, such as bacteria, viruses, and toxins.

If a single tag may be provided that interacts only with a specific chemical species, such as a selected toxin, the tag would only interconnect or interact with the atmospheric sample if the selected chemical agent was present in the atmospheric sample. Otherwise, the tags would not interact with any portion of the atmospheric sample and no detection would occur. Thus, the entire tag population would be uninteracted if no agent was present. Alternatively, a plurality of tag types may be present and interact with a plurality of agent types. For example, a tag type may be present that interacts with each of a selected chemical species, a selected viral species, and a selected bacterial species. Therefore, the tag would interact with each of the selected species, being the chemical, bacteriological, or viral, to allow, for detection of the various species at the selected point. It will be understood that the system 10 may be provided to substantially select or detect a single agent type or a plurality of agent types that may be present in the selected atmospheric sample. Regardless, the analysis and separation sub-system 18 may be able to determine the presence of the selected agents by determining their presence or state of a selected tag. Therefore, the system 10 may be used to determine and detect a plurality of agent types or the presence of only a single agent type.

After the selected agents are tagged, they are generally provided to the separation and analysis of sub-system 18. The analysis and separation sub-system 18 may be any appropriate analysis and separation sub-system depending upon selected characteristics of the aerosol detection system 10. For example, if a liquid is used as a carrier fluid of the selected sample, including the tags and the selected agents, the analysis and separation sub-system 18 may include a substantially liquid based separation, such as various chromatographies, dielectrophoresis, mass discrimination technologies or gel separations systems. Alternatively, if the sample is carried in substantially dry fluid, for example dry air or other inert gas such as argon, the separation and analysis system 18 may be a substantially dry separation and analysis system. Therefore, the separation and analysis system is not intended to be limited by the following description. Simply, a substantially dry separation and analysis system is intended as an exemplary embodiment and not intended to limit the scope of the appended claims.

Figure 3:
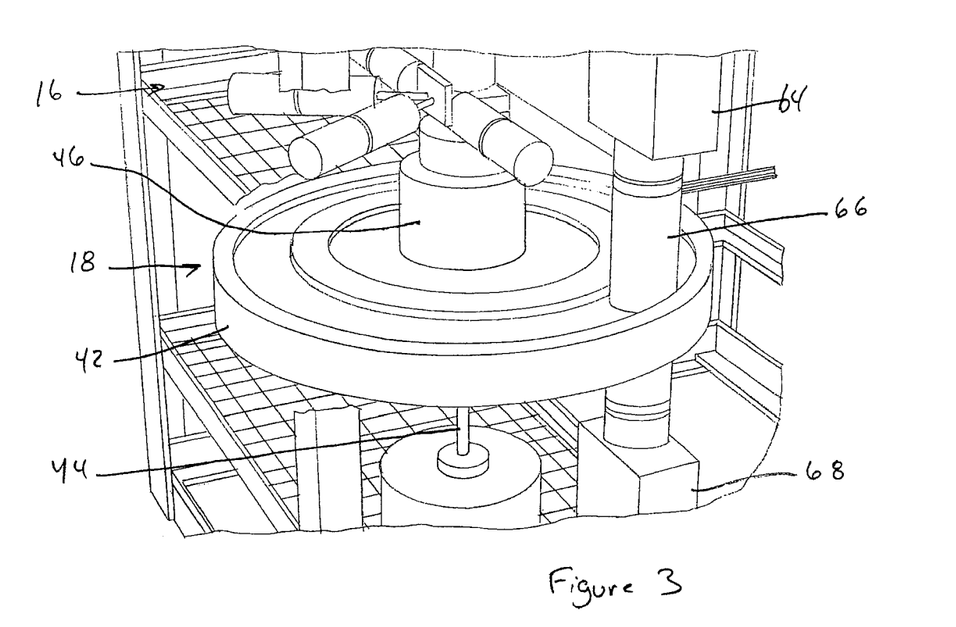
FIG. 3 is a detailed perspective view of the mixing sub-system and the separation and detection sub-system according to an embodiment.
Figure 4:
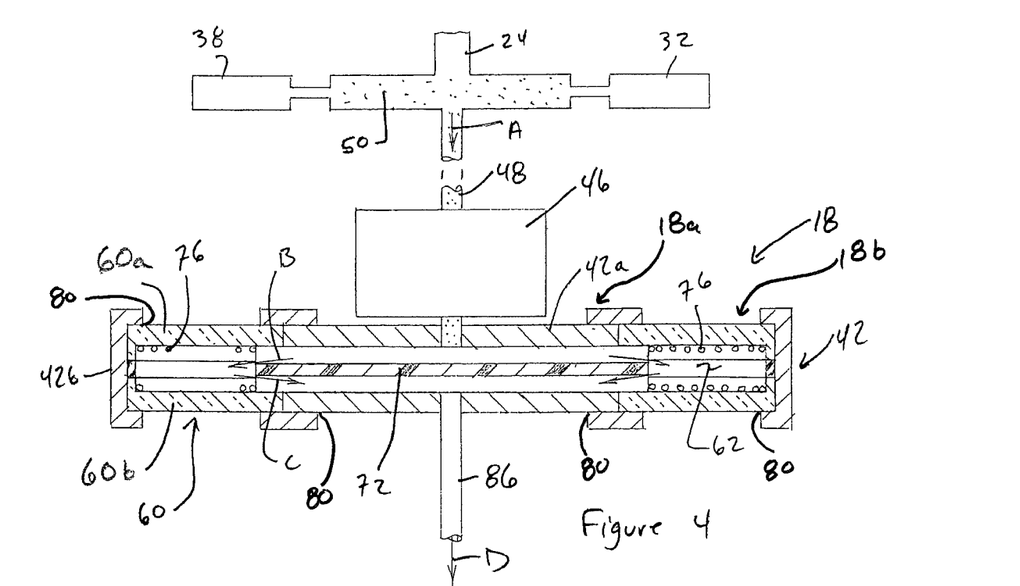
FIG. 4 is a schematic plan view of the mixing and separation and analysis sub-systems according to an embodiment of the present invention.

With reference to FIGS. 3 and 4, the analysis and separation sub-system 18, according to a selected embodiment, is illustrated and described. It will be understood that the separation and analysis sub-system may be substantially a single system and is described in various portions for clarity alone. Therefore, the analysis and separation sub-system 18 generally includes the separation portion 18a that has a separation chamber 42 that defines a substantially annular or toroidal chamber. The separation chamber 42 is able to rotate around a selected axis that is aligned with a spindle or axle 44. The axle 44 allows the separation chamber 42 to spin at a selected rate, while being driven by a motor 46. The motor is able to spin the separation chamber 42 in a selected manner in a selected time.

A first aerosol or inlet conduit 48 is provided to allow the sample and tags to enter the separation chamber 42. Generally, a particle 50 is formed by the interacted tags and the uninteracted tags that travel from the mixing chamber 26 through the inlet conduit 48 to enter the separation chamber 42. As discussed above, the transfer may also be performed with a fluid conduit. For example, if the particles 50 are suspended substantially in a liquid fluid, the separation chamber may be interconnected with a substantially liquid conduit medium. However, as illustrated here, if the separation chamber 42 is a substantially dry chamber, the particles 50 may be provided in a substantially dry fluid.

The inlet conduit 48 allows for the particles 50, including the agent that is interconnected with the tag to be transferred into the separation chamber 42. The conduit 48 is generally provided along the axle or within the axle 44 about which the separation chamber 42 is able to spin. Therefore, the transfer of the particles 50 from the mixing chamber 26 to the separation chamber 42 is substantially unaffected by the operation of the system 10.

Once the particles 50 have been provided to the separation chamber 42, the separation and analysis process may occur. Generally, the separation chamber 42 includes at least one substantially transparent portion 60. The transparent portion 60 or also referred to as an optical window 60 includes any appropriate portion that is transparent to selected wavelengths of energy. The optical window 60 is generally also an annular ring that defines a selected circumference or portion of the separation chamber 42. As discussed above, the separation chamber 42 is exemplary substantially an annular disc and the optical window 60 generally defines a portion of the annular disc of the separation chamber 42. Also, the separation chamber 42 includes a selected thickness, thereby defining an internal separation area 62. The optical window 60 defines at least a portion of the separation area 62. Therefore, the particles 50 will be able to be present between two portions, a first portion 60a and a second portion 60b of the optical window 60.

The optical window 60 (i.e. the first portion 60a of the optical window 60) allows for an excitation source 64 to form or transmit an excitation beam 66 to be transmitted through the optical window 60. The excitation beam 66 excites a selected portion of the particles 50, as described further herein. In addition, a receiver or analysis system 68 is provided to receive or detect through the optical window 60 (i.e. the second portion 60b of the optical window 60) any emitted energy or beam from the selected particles 50, also described further herein. Therefore, the optical window 60 is able to allow both the excitation beam 66 and emitted energy from the selected particles 50 to reach the optical detector 68.

It will be understood that the excitation source 64 may create any appropriate excitation energy 66 that is able to reach the particles 50. Similarly, the particles are able to emit any appropriate energy that is detected by the detector 68. Therefore, an optical range is merely exemplary and not intended to be limiting. For example, the excitation source 64 may emit energy in the infrared portion of the spectrum, while the detector 68 is able to detect wavelengths substantially in the visual spectrum. Alternatively, the excitation source 64 may be able to excite the particles with ultraviolet energy, while the detector 68 detects visible or infrared wavelengths.

It will also be understood that a plurality of separate excitation sources and/or a plurality of detectors may be provided depending upon the selected wavelengths. Alternatively, the excitation source 64 may be able to emit a plurality of wavelengths and the detector 68 able to detect a plurality of emitted wavelengths. Therefore, only requiring a single system that is able to detect or emit various and several wavelengths.

Generally, the detector 68 is also able to discriminate amongst various wavelengths of emitted energy. Therefore, the detector 68 is able to discriminate between, for example, 500 nanometers, 560 nanometers, and 620 nanometers. The detector 68 is able to detect various emitted wavelengths that may be within a general range of the electromagnetic energy spectrum.

Extending from the optical window 60 and generally towards the axle 44 is an insulator portion 72. The insulator portion 72 is able to interconnect the optical window 60 through the center of the separation chamber 42 and connect at the optical window 60 to the axle 44 for rotation of the separation chamber 42. Also, the insulator 72 substantially electrically isolates a dielectric pattern or electrode 76 that is provided near the optical window 60. The electrode 76 is able to provide a voltage over the area of the separation chamber 42. The dielectric electrode 76 is able to provide a dielectric force to the particles 50 that are provided to the separation area 62. As described herein, the voltage provided by the electrode 76 interacts with a centrifugal force that is produced by rotation of the separation chamber 42. Also, various seals 80 are provided to insure that the sample of the atmosphere that is interconnected with the tags to form the particles 50 are not able to contaminate or be contaminated from external sources or from the system 10 itself. The seals can also ensure the particles 50 do not escape the separation area 62. Therefore, the seals 80 are able to insure that the sample that has been collected and interconnected with the tags to form the particles 50 is able to be separated and detected using the separation system 42.

The detection system 10, described above, may include various selected or appropriate components for the various portions of the system 10. Nevertheless, generally the system 10 is able to provide for collection, concentration and detection of various or selected agents that may be present in an atmospheric sample. Various exemplary applications, will now be discussed for illustration of a selected embodiment of the invention. It will be understood that the following description is not intended to limit the scope of the system 10, nor be exclusive of other appropriate applications or subsystem portions for the detection system 10.

According to an embodiment, the tags included in the tagging subsystem 16 interact with the selected agents and form the particles 50 may include a selected size or mass. Generally, the tags are in a substantially powder form that can be easily mixed with the selected volume of the atmospheric sample. The tags may include any appropriate selected properties. For example, the tags may be phosphorescent or emit energy under selected irradiation or excitation energies. The tags, and the particles 50, may luminesce or emit energy of a selective wavelength when excited with a selected wavelength of energy.

The phosphors may be substantially "up-converter phosphors" that emit energy at a wavelength higher than the wavelength of the energy used to excite the particles 50. The particles may be excited with infrared radiation, that is emitted from the excitation source 64, to, in turn, emit energy in a substantially visual wavelength. Therefore, the particles 50 may be excited with energy at a wavelength generally about a wavelength above about 900 nanometers. Yet emit energy in a wavelength of less than about 900 nanometers. Therefore, the wavelength or energy of the photon emitted is substantially up-converted from the energy the photon used to excite the particle 50. It will be understood, however, that the particles may be excited by any appropriate wavelength and emit any appropriate wavelength to be detected by the detector 68. In addition, the tags may include other appropriate properties that may be detected with the detector 68.

Furthermore, the tags need not simply be a solid or large particle that interacts with the agent from the atmospheric sample. A single chemical species may be provided that can interact with the selected agent. The selected chemical species may also phosphor or emit a selected radiation when excited with a different selected radiation.

Nevertheless, the tags may be provided at a selected size and mass as well. The tags may be selected to include a size that is substantially equivalent or greater than the size and/or mass of a selected agent to be detected with the tag. The tag may be provided at about 0.1 microns to about 1 micron for interaction with agents, including bacteria or spores. Alternatively or in addition, smaller tags, such as tags of about 0.1 and smaller microns may be provided to interact with other selected agents, such as viruses or chemical toxins. Therefore, the selected size and mass may be selected for various attributes or characteristics of the system 10.

The tags are able to or formed to interact with the selected agents, including the various phosphor properties. For example, the surface of the particle may include an antibody that is able to interact with the bacteria or virus. Similarly, the tag may include a receptor site that is able to interact with a chemical toxin agent that may be present in the atmospheric sample. The coating or receptor site on the tag may be substantially specific to a single agent or to a group of agents. For example, the coating may interact with any of a selected family of bacteria or only interact with a selected specific bacteria. Regardless, the tag, when mixed with the atmospheric sample in the mixing chamber 26, is able to substantially interact with the selected agent for later analysis and separation.

Generally, the tag including a selected coating, may substantially bind a bacteria that may be present in the selected atmospheric sample. Therefore, the tag is substantially fixed or bound to the bacterial agent, forming an interacted tag or bound tag, for later separation and detection. Also, the tag may include a selected and specific emission wavelength. The tag may be used to detect the presence of a selected agent by determining the presence of the selected wavelength in the detection chamber 18. The selected and known wavelength of the tag, when bound to only a selected agent, is used to detect that specific agent by detection of the known and selected wavelength.

As discussed above, the various tags may be provided in the system in a selected moving fluid. It will be understood that the fluid may be either a gas, which is substantially dry, or a liquid. In addition, the gas may include a selected amount of moisture or liquid, depending upon various characteristics of the detection system 10. Therefore, the tags may be selected depending upon the fluid, which is used to transfer the atmospheric sample. In addition, the specific probe, that binds or interacts with the agent, on the tag may be selected depending upon the fluid used to transfer the atmospheric sample.

Tags in the tagging subsystem 16 may also include other selected characteristics. For example, the tags may include a selected known dielectric constant, which is substantially different than that of the agent selected to interact with the selected tag. Therefore, the dielectric constant may be used in conjunction with the electrode 76 to achieve a selected separation of the particles 50 within the separation chamber 42. For example, the tag may include a dielectric constant, which is different than that the agent itself, such that the difference in dielectric constant between the tag plus the agent and the agent by itself will be substantially different when acted upon by the selected forces. In addition, the tag may be selected to alter the density of the agent in conjunction with the tag as opposed to the agent alone. Therefore, interaction of the tag or particle tag with the agent to form the particles 50 substantially alters or produces a selected constant, including a dielectric constant and density, for later use in the separation chamber 42.

In operation of the separation chamber 42, the particles 50 are allowed to move from the mixing chamber 26 in the direction of arrow A towards the separation chamber 42. The particles 50 enter the upper portion 42*a* of the separation chamber 42 for separation. As discussed above, the separation chamber 42 generally rotates, thereby providing a centrifugal force on the particles 50. That is, the particles 50 are generally forced towards an outside 42*b* of the selection or separation chamber 42. The particles 50 are forced towards the outside 42*b* in the direction of Arrow B, or the edge of the annular or toroidal separation chamber 42. Alternatively, or contrary to the centrifugal force B, the dielectric force forces the particles in the direction of arrow C. The dielectric force, which is produced by the voltage provided across the electrode 76, forces the particles 50 towards the center, towards the axle 44 (which can define a center axis) of the separation chamber 42. The two forces, as discussed briefly herein, are dependent upon the dielectric constant of the particle 50 and the mass and size of the particle 50. Very briefly, the particle 50, having a selected mass, will include a force that is towards the outside 42*b* of the separation chamber 42 because of the centrifugal force. Whereas, the dielectric constant of the particle provides a contrary force the direction of arrow C towards the center of the separation chamber 42. Nevertheless, after the particles 50 have been generally separated and detected, the particles continue in the direction of arrow D through an outlet conduit 86.

After the particles 50 have been separated and the detection completed, the separation chamber 42 may be cleared by removing the particles therefrom. In addition, plasmas may be created within the separation chamber 42, for example, using the electrode 76, to substantially clean in the separation chamber 42 for analysis of a second or additional sample. In this way, the system 10 is generally self-cleaning for a fast cycle to a second analysis procedure.

In operation of the separation chamber 42, various forces are used to separate the particles 50 in an efficient manner. For example, various centrifugal and dielectric forces are applied to particles 50 to separate the particles 50 in a selected manner or in a selected time period. For example, in spinning the separation chamber 42 on the axle 44, a centrifugal force is applied to the particles 50 generally defined by equation 1:

$$\vec{F}_C = \hat{r} \cdot m r \omega^2 \qquad \text{EQ. 1}$$

where r-hat is the unit vector along the radius r, m is the particle mass, and w is the angular frequency. Therefore, the force on the particle 50, depending upon the selected particle 50, can be determined with Eq. 1.

Similarly, a dielectric force is produced on the particle 50 by providing voltages with the electrode 76. As discussed above, the dielectric force is substantially opposite the centrifugal force to assist in separation of the particles 50. Nevertheless, the dielectric force is, generally assuming that the particle 50 does not appreciably change the applied external electrical field and differentiating generally known equations provides that the dielectric force is given by equation 2:

$$\vec{F}_D = -\nabla W = \frac{\varepsilon_1 - \varepsilon_0}{8\pi} V_P \nabla^2 (\vec{E} \cdot \vec{E}) \qquad \text{EQ. 2}$$

where W is the energy stored in the particle when a particle 50 is in the field and $V_p$ is the volume of the particle 50.

In addition, the particle 50 is generally placed within a fluid. As discussed above, the fluid may be a substantially dry gas, although it may also be a liquid. Therefore, a viscous force is also generally present and is able to act upon the particle 50. The viscous force is given by the equation 3:

$$\vec{F}_v = -\frac{1}{2}\rho|\vec{V}_{Rel}|^2 C_D A_P \frac{\vec{V}_{Rel}}{|\vec{V}_{Rel}|} \quad \text{EQ. 3}$$

where $V_{REL}$ is the particle velocity relative to the gas, ρ is the gas density, $C_D$ is the drag co-efficient, and $A_p$ is the particle cross-section area. The $V_{REL}$ is approximately one centimeter per second, in the gas. The drag co-efficient is generally given by the Reynolds number, which is defined by a equation 4:

$$R = \frac{V_{Rel} d_p \rho}{\mu} \quad \text{EQ. 4}$$

where $d_p$ is approximately $10^{-4}$ cm and μ is the viscosity of the gas. Generally, when the particles are substantially small, the particles will be entrained completely within the gas. This is even more so when the fluid is a liquid which has a much higher viscosity. Finally, a hydrostratic force of the fluid, which is generally produced as the separation chamber 42 rotates, is defined by equation 5:

$$\frac{dp}{dr} = \rho(r)\omega^2 r \quad \text{EQ. 5}$$

where r is the radius of the separation chamber 42. The state of a perfect gas is generally defined by equation 6:

$$\rho = \frac{p}{\Re T} \quad \text{EQ. 6}$$

where p is the gas pressure, T is the gas temperature, and R, the gas constant, is defined by ergs/K° gr.

Under exemplary conditions where r is approximately 10 cm, the temperature is approximately 300 Kelvin, and ω is approximately 103 radians per second, the density of the fluid will not increase greatly. However, it will be understood, that if the fluid is a different fluid, such as a liquid, the hydrostatic forces may be substantially different. Nevertheless, the hydrostatic force for the gas may be defined by equation 7:

$$\vec{F}_H = -\hat{r}\cdot\rho(r)\omega^2 r V_\rho = -\hat{r}\cdot\rho(r=r_0)e^{\frac{\omega^2}{2\Re T}(r^2-r^0)}\omega^2 r V\rho \quad \text{EQ. 7}$$

Therefore, the motion or forces acting upon the particles 50 while they are in the separation chamber 42 is generally defined by equation 8:

$$m\ddot{r} - mr\dot{\theta}^2 = F_c + F_D + F_V + F_H \quad \text{EQ. 8}$$

Using the equations defined above, and generally known mathematical techniques, various simulations may be used to test the theoretical operation of the system 10 to determine a theoretical separation of the particles 50 of a selected density and including a selected dielectric constant. Nevertheless, the equations and the theory simply define the actions which separate the particles 50 in the separation chamber 42. That is, after the particles 50 are introduced into the separation chamber 42, the centrifugal force produces a first force, which moves the particles 50 generally in the direction of arrow B. The dielectric force, however, forces the particles 50 in the direction of arrow C. Therefore, the two forces are acting substantially opposite one another.

Generally, the system 10 determines the presence of an agent by determining the presence of differences between the presence of an interconnected tag and the presence of the tag alone. Therefore, once an agent has interconnected or combined with a tag its dielectric force and/or mass changes compared to the tag alone. For example, a virus alone may have a density of about 1.46 grams per $cm^3$ and a dielectric constant of about 7. Whereas a virus interacted with a selected tag may have a density of about 2.25 grams per $cm^3$ and a dielectric constant of about 6. Therefore, the density and dielectric constant of the agent alone compared to the agent interacted with the tag may be used to separate and determine the presence of an agent in the atmospheric sample. The size, density, and dielectric constant of the tag could be selected appropriately to maximize the difference in mass and dielectric constant and thus affect better separation between the interconnected tag and the tag alone.

After the tags have been combined with the agents in the mixing chamber 26, the various constants of the agent have changed. Therefore, in the separation chamber, the tags alone (uninteracted tags) and the interacted tags can be separated. As discussed above, the tags include a particular characteristic that can be detected using the detector 68. Therefore, if the tag is able to emit a selected energy at a selected wavelength when excited, it is able to do so whether or not an agent is interacted with the tag. Therefore, if the particles 50 are separated in the separation chamber 42 and the tags have interconnected with a selected agent, then two groups of a single tag with a single characteristic will be present.

For example, if a tag emits energy at a wavelength of approximately 460 nanometers when excited with the excitation beam 66, it will do so within the separation chamber 42. During the separation process, within the separation chamber 42, the two species or groups of particles, one which is interconnected with the tag, and one where the tag is uninteracted, will be produced, if a selected agent is present. However, if no selected agent is present, then only one group will be formed, that is the tag will substantially not separate into more than one group because the tag or all particles 50 are substantially uniform. Therefore, during the detection process, a single group only will include the selected characteristic, thereby notifying or allowing for the determination that the tag alone is the only particle 50 present and thus allowing for a negative determination on that selected agent.

If, however, more than one group with the selected emitted energy or characteristics is found, then it will be determined that the agent is present. The presence of two groups is notice that at least one group has been altered, due to the presence of an agent. Simply, the tag will only bind to the agent, thereby only the presence of the agent will alter the characteristics of the tag, such that it will be separated from a second group in the separation chamber 42.

It will be understood that the separation chamber 42 may be any appropriate separation chamber, as discussed above. Regardless of the type of separation chamber 42, the separation chamber 42 is able to separate the population of a particular tag, depending upon whether a particular agent has connected to the tag. Therefore, the presence of two populations, including a single characteristic, such as a light emitted at a particular wavelength or a particular separation in a column or allows for a positive determination of a presence of an agent.

Using the above described mechanisms, the system 10 may be used to collect, concentrate, separate, and determine presence of an agent in approximately one minute. The presence of both the centrifugal force and the dielectric force allow for a substantially quick separation of the particles 50 within the gas fluid. It will be understood that other fluids may allow for a quicker separation or only require a single separation force, such as a centrifugal force or a dielectric force, to achieve the selected separation. In addition, a longer detection time or analysis time may be used, such that only one force is necessary to separate the particles into various groups. Therefore, it will be understood that the above description is merely exemplary and not intended to limit the scope of the appended claims.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method of determining the presence of a selected agent in an atmospheric sample with a system including a sample collector, a sample tagger, a sample separator, and a detection component, the method comprising:
- collecting an atmospheric sample of a selected size of an atmosphere;
- mixing a tag with the atmospheric sample;
- forming a volume including at least one of an interacted tag and an uninteracted tag;
- forcing the formation of a collection from the volume of at least one of the interacted tag and the uninteracted tag;
- detecting the presence of the collection of at least one of the interacted tag and the uninteracted tag; and
- outputting the result of the detection;
- wherein an interacted tag is formed generally only in the presence of a selected agent.

2. The method of claim 1, further comprising collecting the selected agent from the collected atmospheric sample for mixing with a tag.

3. The method of claim 2, further comprising:
- concentrating the selected agents from the atmospheric sample for mixing with a tag.

4. The method of claim 1, wherein mixing a tag with the atmospheric sample includes:
- generally contacting the tag with the selected agent from the atmospheric sample.

5. The method of claim 1, wherein forming a volume including at least one of an interacted tag and an uninteracted tag includes:
- binding the tag to the selected agent to form the interacted tag.

6. The method of claim 1, wherein forcing the formation of a collection from the volume of at least one of the interacted tag and the uninteracted tag includes:
- separating said interacted tag from said uninteracted tag using a mass differential between said interacted tag and said uninteracted tag.

7. The method of claim 1, wherein forming a volume including at least one of an interacted tag and said uninteracted tag includes:
- separating said interacted tag from said uninteracted tag based upon a dielectric constant differential between said interacted tag and said uninteracted tag.

8. The method of claim 1, wherein forcing the formation of a collection of at least one of an interacted tag in said uninteracted tag includes:
- separating said uninteracted tag from said interacted tag using both a mass separation and a dielectric force separation.

9. The method of claim 1, wherein forming the uninteracted tag includes not contacting the tag with the selected agent.

10. The method of claim 1, wherein detecting the presence of the collection includes:
- exciting said tag to force said tag to form an emission energy; and
- detecting the emission energy from the excited tag.

11. The method of claim 10, further comprising:
- determining the presence of more than one collection;
- wherein the presence of more than one collection allows for a determination of the presence of the selected agent.

12. The method of claim 1, wherein outputting the result of the detection includes outputting the presence of one or more collection.

13. The method of claim 1, wherein collecting an atmospheric sample includes collecting a plurality of types of the selected agent;
- wherein each of the type of selected agent relates to a selected detectable species.

14. The method of claim 12, wherein mixing a tag with the atmospheric sample includes:
- mixing a plurality of types of tags with the plurality of types of selected agents;
- wherein each of the types of the plurality of tags interacts with substantially only a single type of the plurality of selected agents to form a plurality of types of interacted tags.

15. The method of claim 1, wherein forcing the formation of a collection from the volume includes forming a formation of a collection in a fluid that is substantially dry.

16. The method of claim 1, wherein said tag is an up-converter.

17. The method of claim 1, further comprising:
- inducing an emission of a first wavelength from at least one of said interacted tag and said uninteracted tag with a second wavelength;
- wherein said first wavelength is less than said second wavelength.

18. A method of determining the presence of a selected agent in an atmospheric sample with a system including a sample collector, a sample tagger, a sample separator, and a detection component, the method comprising:
- collecting an atmospheric sample of a selected size of an atmosphere;
- providing at least a portion of the atmospheric sample to a mixing cell;
- injecting from at least a single injector a tag into the mixing cell;
- mixing the injected tag with the at least a portion of the atmospheric sample;
- forming a volume including at least one of an interacted tag and an uninteracted tag;
- moving the volume to a separation system;
- determining the identity of at least one constituent of the at least a portion of the atmospheric sample at least in part by separating the interacted tag and the uninteracted tag; and
- outputting the result of the determination;
- wherein an interacted tag is formed generally only in the presence of a selected agent.

19. The method of claim 18, further comprising:
providing a plurality of the injectors; and
injecting a tag from at least one of the plurality of injectors into the mixing chamber.

20. The method of claim 18, further comprising:
concentrating the selected agents from the atmospheric sample for mixing with a tag.

21. The method of claim 18, wherein determining the identity of at least one constituent of the at least a portion of the atmospheric sample includes:
separating said interacted tag from said interacted tag using a mass differential between said interacted tag and said uninteracted tag.

22. The method of claim 21, wherein separating includes:
forming a separation chamber that defines a substantially annular chamber;
moving the volume to the separation chamber; and
rotating the separation chamber around a selected axis.

23. The method of claim 18, wherein forming at least one of an interacted tag and said uninteracted tag includes:
separating said interacted tag from said uninteracted tag based upon a dielectric constant differential between said interacted tag and said uninteracted tag.

24. The method of claim 1, wherein forcing the formation of a collection of at least one of an interacted tag in said uninteracted tag includes:
separating said uninteracted tag from said interacted tag using both a mass separation and a dielectric force separation.

25. The method of claim 18, further comprising:
forming a separation chamber;
providing an optical window;
transmitting energy from an excitation source through the optical window;
exciting a selected portion of the volume.

26. The method of claim 25, further comprising:
providing a receiver; and
receiving an emitted energy the volume with the receiver.

27. A method of determining the presence of a selected agent in an atmospheric sample with a system including a sample collector, a sample tagger, a sample separator, and a detection component, the method comprising:
collecting an atmospheric sample of a selected size of an atmosphere;
providing at least a portion of the atmospheric sample to a mixing cell;
injecting from at least a single injector a tag into the mixing cell;
ultrasonically mixing the injected tag with the at least a portion of the atmospheric sample;
forming a volume including at least one of an interacted tag and an uninteracted tag;
moving the volume to a separation system;
separating the volume by spinning the volume in a separation device causing the interacted tag to be separated from the uniteracted tag and both moving to an area including a transmission window, wherein two groups of particles are formed if a selected agent is present, a first group of particles that includes the interconnected tag and a second group of particles that includes the uninteracted tag;
providing an excitation source to transmit energy through the transmission window to excite at least a portion of the interacted tag or the uninteracted tag;
receiving an emission from at least a portion of the interacted tag or the uninteracted tag;
determining the presence of one or more groups of particles; and
outputting the result of the determination.

* * * * *